United States Patent [19]
Lindemann et al.

[11] Patent Number: 4,874,382
[45] Date of Patent: Oct. 17, 1989

[54] SAFETY SYRINGE

[75] Inventors: Peer Lindemann, West Bend; Victor M. Haughton, Dousman, both of Wis.

[73] Assignee: Servetus Partnership, Milwaukee, Wis.

[21] Appl. No.: 109,189

[22] Filed: Oct. 15, 1987

[51] Int. Cl.$^4$ .............................................. A61M 5/00
[52] U.S. Cl. ...................................... 604/195; 604/198
[58] Field of Search ............... 604/198, 196, 195, 194, 604/187, 263, 228

[56] References Cited
U.S. PATENT DOCUMENTS

| | | | |
|---|---|---|---|
| 2,722,215 | 11/1955 | Dahlgren | 604/228 X |
| 2,841,143 | 7/1958 | Bertram. | |
| 3,825,003 | 7/1974 | Kruck. | |
| 4,009,716 | 3/1977 | Cohen. | |
| 4,573,976 | 3/1986 | Sampson et al. | 604/198 |
| 4,664,259 | 5/1987 | Landis. | |
| 4,676,783 | 6/1987 | Jagger et al. | |
| 4,747,831 | 5/1988 | Kulli | 604/198 |
| 4,767,413 | 8/1988 | Haber et al. | 604/232 X |

Primary Examiner—John D. Yasko
Attorney, Agent, or Firm—Andrus, Sceales, Starke & Sawall

[57] ABSTRACT

A safety syringe includes a protective sheath disposed within the interior of the body portion of the syringe. A needle extends from the body portion of the syringe when the syringe is in an armed condition. A biasing mechanism, such as a stretched coiled spring, is connected to the upper end of the needle and tends to draw the needle into the protective sheath. A releasable retainer mechanism engages a detent formed on the upper end of the needle to retain the needle in its extended position against the biasing force of the spring. After use, the releasable retainer mechanism is actuated either by the user or in response to movement of the syringe plunger, to release the detent formed on the needle and to cause the needle to be withdrawn into the protective sheath to prevent accidental contact with the sharpened end of the needle. In another embodiment of the invention, a telescoping sheath is held in a retracted condition adjacent the hub of the needle by a releasable retainer mechanism against the force of a biasing mechanism, such as a compressed coil spring. After use of the needle, the releasable retainer mechanism is actuated to effect extension of the telescoping sheath and to thereby enclose the needle to prevent accidental contact therewith.

19 Claims, 7 Drawing Sheets

SAFETY SYRINGE

BACKGROUND AND SUMMARY

This invention broadly relates to a medical device, and more particularly a medical device for administering or receiving fluids to or from a patient.

Health care personnel using needles for injecting or for withdrawing blood are subject to serious risk of infection if they are accidentally scratched or punctured by a needle after its use. Such a scratch or puncture carries with it the risk of incurring a viral or bacterial infection.

It is estimated that there are, on the average, 50 to 100 accidental needle stick injuries per hospital per month. It is further estimated that such accidental injuries often necessitate examination and laboratory testing costing between $700.00 and $1000.00 per injury. An infection caused by such an accidental needle stick injury leads to even greater expense and disability.

Because of the substantial risk and cost associated with accidental needle stick injuries, procedures have been developed for disposing of used hypodermic syringes and/or needles. One procedure is to remove the needle from the syringe and dispose of it separately in a receptacle designed for needle disposal. In some cases such removal of the needle requires a special implement, such as a guillotine-like mechanism which severs the needle from the syringe and deposits the needle in a closed receptacle. However, the receptacle and the implement needed to remove the needle are usually not available at the bedside, where many injections are made. Thus, this procedure is inadequate to prevent accidental needle sticks and resulting infection in such cases.

One mechanism for protecting a needle after use is shown in U.S. Pat. No. 4,664,259 to Landis. This patent discloses a container for enclosing a needle after use. The structure of the Landis patent requires a person to manually place the container over the needle after use by pivoting the container onto or about the needle. Such action requires the person to bring his or her fingers into close proximity with the tip of the needle, thus creating the potential for accidental contact with the needle tip. The enclosure provided by the container of the Landis patent does not prevent reuse of the syringe, since a person need only remove the container to once again expose the needle for use.

U.S. Pat. No. 4,676,783 to Jagger et al. discloses an assembly for disabling an intravenous cannula after use. The structure shown in the Jagger et al. patent requires the user to manually withdraw the needle into a cylinder, upon which the tip of the needle is enclosed to prevent accidental contact therewith. This structure is not for hypodermic use; and does not prevent a person from reusing the intravenous cannula.

The present invention overcomes the shortcomings of previous mechanisms and/or procedures for preventing accidental contact with the tip of a needle after use. In particular, an object of the present invention is to provide a structure for automatically or semi-automatically disarming or disabling a needle after use. A further object of the invention is to provide such a structure which automatically or semi-automatically disarms or disables a needle without the user bringing his or her fingers into the vicinity of the tip of the needle. Yet another object of the invention is to provide a structure for automatically or semi-automatically disarming or disabling a needle immediately upon withdrawal of the needle from the patient or even while the needle is still in the patient, so that the tip of the needle is never exposed after withdrawal from the patient. Yet another object of the invention is to provide a structure which permanently disarms or disables a needle after use to effectively prevent reuse of the needle, whether accidental or intentional.

In accordance with the invention, a medical device for administering or receiving a fluid to or from a patient, such as a hypodermic syringe, has a conduit means extending therefrom, such as a needle. The needle has a sharpened end adapted for insertion into a patient for allowing fluid, such as medication, to flow between the syringe and the patient. A disarming means is provided for converting the syringe from an armed condition wherein the sharpened end of the needle is exposed, to a disarmed condition wherein the sharpened end of the needle is covered, so as to prevent contact with the end of the needle after use. The disarming means includes means for urging the syringe toward its disarmed condition, and a releasable retainer means for retaining the medical device in its armed condition during use and for releasing the means urging the medical device toward its disarmed condition after use. In this manner, the syringe is caused to be converted to its disarmed condition after use.

In one embodiment, the hypodermic syringe is provided with an internal silo, and the means for urging the syringe toward its disarmed condition comprises a biasing means, such as a stretched coil spring, tending to draw the needle into the silo. The releasable retainer means comprises a catch or other mechanism for retaining the needle in an extended position, so as to maintain the syringe in its armed condition against the biasing force provided by the coil spring. After the syringe has been used and its contents injected into the patient through the needle, the catch is released, so as to allow the needle to be withdrawn into the silo by the spring and the syringe to be converted to its disarmed condition. Various mechanisms for releasing the catch are disclosed, including semi-automatic mechanisms manually actuable by the user after completion of the injection, as well as automatic mechanisms responsive to movement of the syringe plunger for automatic actuation upon completion of the injection.

In another embodiment, a telescoping sheath comprising a plurality of segments is provided adjacent the hub of the needle. The segments of the telescoping sheath are held in a retracted condition by the releasable retainer means, to keep the needle exposed during use. The means for urging the syringe toward its disarmed condition comprises a biasing means, such as a compressed coil spring, tending to urge the telescoping sheath outwardly toward its extended condition so as to cover and enclose the tip of the needle. The releasable retainer means comprises a gripping mechanism for engaging the end portions of the segments of the sheath to retain the sheath in its retracted condition against the force of the compression spring. After the syringe has been used and its contents injected into the patient through the needle, the gripping mechanism is released so as to allow the segments of the telescoping sheath to project outwardly to their extended condition so as to enclose the needle. In its extended condition, the telescoping sheath covers the tip of the needle after use to prevent accidental contact therewith.

In both embodiments, the releasable retainer means can be actuated either automatically in response to the action of the plunger or semi-automatically in response to manual actuation by the user. The releasable retainer means can be actuated while the needle is in the patient, so that the top of the needle is never exposed after withdrawal from the patient.

BRIEF DESCRIPTION OF THE DRAWINGS

The drawings illustrate the best mode presently contemplated of carrying out the invention.

In the drawings.

DETAILED DESCRIPTION

Figures 1, 2, 3:
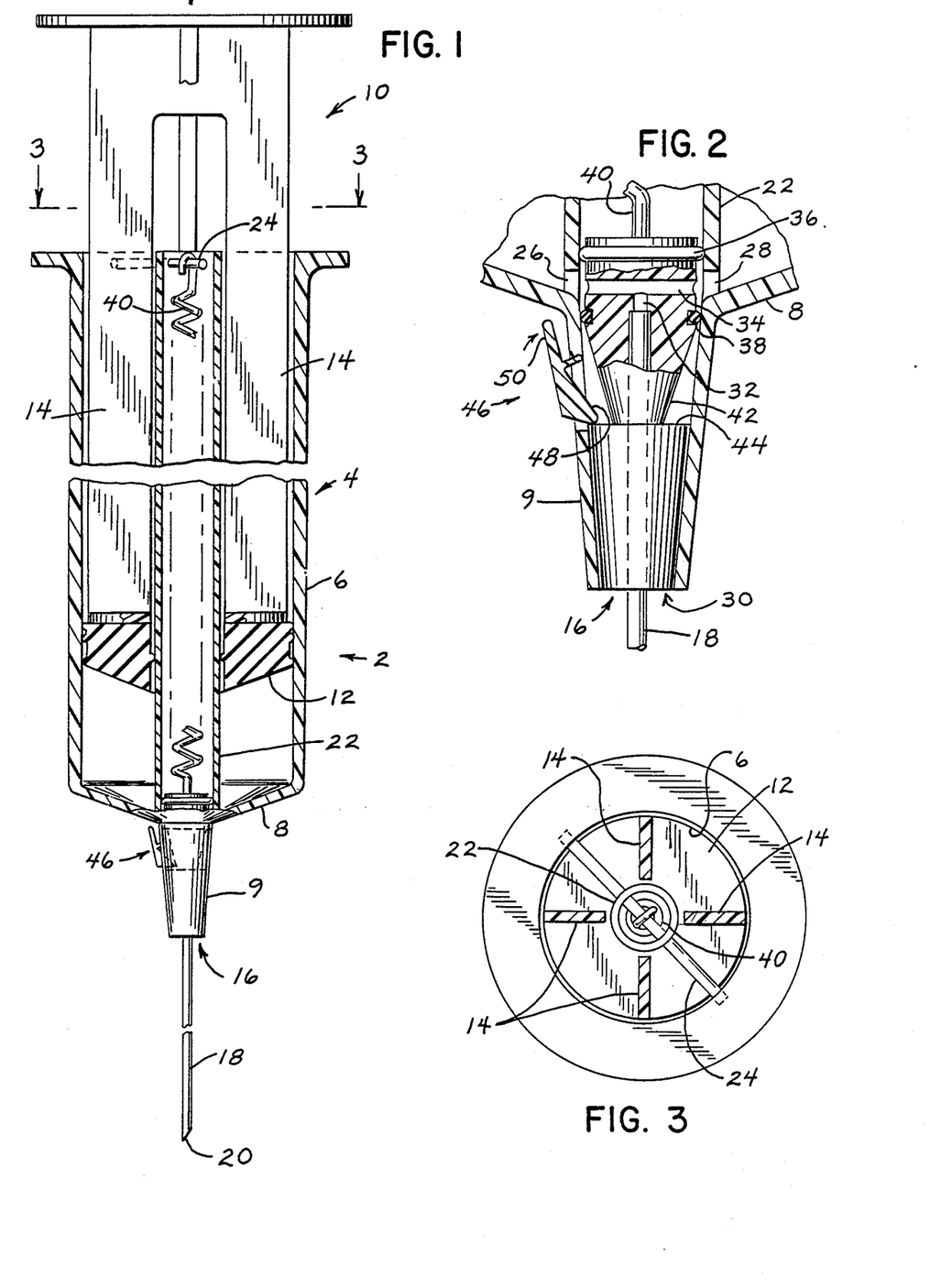
FIG. 1 is an elevation view partially in section of a syringe constructed according to the invention in its armed condition with the needle extended, showing a semi-automatic release mechanism.
FIG. 2 is an enlarged sectional view of a portion of the syringe of FIG. 1, showing the pivotable catch release mechanism retaining the needle in its extended position.
FIG. 3 is a sectional view taken generally along line 3—3 of FIG. 1.

With reference to FIG. 1, a safety syringe 2 includes a cylindrical body portion 4 having a side wall 6 and an end wall 8 at one end thereof. The interior of cylindrical body portion 4 is adapted to be filled with a fluid, such as a medication, to be injected into a patient. A nipple 9 extends from end wall 8 of cylindrical body portion 4. A plunger assembly 10 has a head 12 formed of a resilient material connected to a series of webs 14. As is well known, head 12 of plunger assembly 10 mates with the interior of cylindrical body portion 4 and is slidable therealong to eject medication from the interior of cylindrical body portion 4.

A needle assembly 16 has an elongated hollow needle 18 which extends from nipple 9 of body portion 4. Needle 18 is in fluid communication with the interior of body portion 4, and provides a conduit for passage of fluid ejected from the interior of body portion 4. Needle 18 has a sharpened end 20 adapted for hypodermic or intramuscular insertion, for providing an injection of medication from body portion 4 through needle 18 by means of plunger assembly 10, as is well known.

As a means for disarming syringe 2 after use, a cylindrical silo 22 is provided in the interior of body portion 4. Silo 22 extends longitudinally along substantially the entire length of body portion 4. Silo 22 is affixed at its upper end by means of a pin 24 (FIG. 3) extending across the width of the cylindrical body portion 4 and affixed at either end to side wall 6. Pin 24 extends through openings disposed in either side wall of silo 22. Silo 22 is connected at its lower end to end wall 8, of body portion 4 (FIG. 2). A pair of passages 26, 28 are formed in the lower end of silo 22 adjacent end wall 8, the function of which will be explained. As seen in FIGS. 1 and 3, webs 14 are formed to accommodate the central location of silo 22.

With reference to FIG. 2, needle assembly 16 includes a head or hub portion, generally denoted at 30, from which needle 18 extends. Head portion 30 of needle assembly 16 is adapted to fit within the interior of nipple 9. Head portion 30 has a substantially central longitudinal passage 32, which is adapted to receive the upper end of needle 18 to retain needle 18 therein. Longitudinal passage 32 terminates at a transverse passage 34 extending across the upper end of head portion 30. With this arrangement, medication contained within the interior of body portion 4 of syringe 2 can flow from the interior of body portion 4 through passages 26, 28 in silo 22 and into transverse passage 34 of needle head portion 30. The medication then passes from transverse passage 34 into longitudinal passage 32 and into the hollow interior or lumen of needle 18 to the patient. In this manner, an unrestricted flow path is provided from the interior of cylindrical body portion 4 into the patient.

A pair of resilient sealing rings 36, 38 are provided in a pair of circumferential grooves disposed in the upper end of needle head portion 30. Rings 36, 38 seal silo 22 and nipple 9, respectively, against passage of medication thereto during ejection of medication from syringe 2.

With reference to FIGS. 1 and 2, a coil spring 40 is connected at one end to pin 24 and at the other end to the upper end of needle head portion 30. When syringe 2 is in an armed condition as shown in FIG. 1, where needle 18 is extended for use, coil spring 40 is in a stretched condition so as to bias needle assembly 16 upwardly. Such biasing force urges needle assembly toward silo 22.

Figure 4:
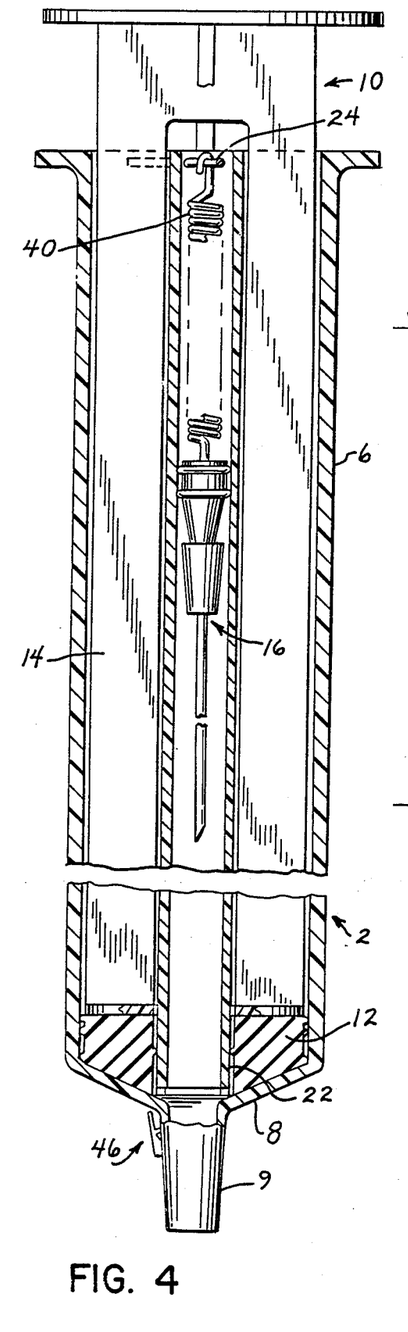
FIG. 4 is an elevation view similar to FIG. 1, showing the syringe after medication has been ejected therefrom and after actuation of the release mechanism, with the needle in its retracted position so that the syringe is in its disarmed condition.

A detent is formed in needle head portion 30, shown in FIG. 2 as an angled circumferential reduced portion 42 forming a shoulder 44. A pivotable catch 46 having a retainer end 48 and a trigger end 50 is pivotably connected to nipple 9. Retainer end 48 of pivotable catch 46 engages shoulder 44 of needle head portion 30 to retain needle 18 in its extended position against the bias of spring 40. This maintains syringe 2 in its armed condition. When trigger end 50 of catch 46 is depressed, retainer end 48 pivots outwardly from the interior of nipple 9 to disengage shoulder 44, thus allowing the biasing force provided by spring 40 to draw needle assembly 16 into silo 22, as shown in FIG. 4. This action disarms syringe 2 and prevents accidental contact with sharpened end 20 of needle 18. In its disarmed condition, syringe 2 has the entire length of needle 18 withdrawn into silo 22, with coil spring 40 in its normal relaxed condition.

As is customary with medical syringes, syringe 2 is shipped in its armed condition with needle 18 extending from body portion 4, with a protective sheath (not shown) installed over needle 18 to prevent accidental contact therewith prior to administration of medication from syringe 2. In operation, the protective sheath covering needle 18 during shipment is removed, and syringe 2 filled with medication in a manner as is well known. Needle 18 is then inserted into the patient, and the medication is injected by depressing plunger 10 to eject the medication from the interior of body portion 4. As above explained, medication passes through needle 18 to enter into the patient's bloodstream or muscle.

After the medication has been administered, needle 18 may either be withdrawn from the patient or left in the patient. If the needle is withdrawn from the patient, accidental contact with sharpened end 20 of needle 18 which breaks the skin will pass any infectious agent on the needle from the patient to the person making such contact with the needle. Thus, immediately after withdrawal of the needle from the patient the syringe should be placed in its disarmed condition. To do so, the user depresses trigger end 50 of catch 46 to release needle assembly 16 and thereby allow needle 18 to be withdrawn into silo 22. As can be seen, a person may depress trigger end 50 of catch 46 while keeping his or her fingers a clear, safe distance from sharpened end 20 of needle 18 to minimize the potential for contact therewith. In such a disarmed condition, accidental contact with sharpened end 20 of needle 18 is prevented.

Alternatively, the person administering the injection may leave the needle in place in the patient after the injection is completed. In this case, with the needle still in the patient, the administrator depresses trigger end 50 of catch 46 to release needle assembly 16. This action allows needle 18 to be withdrawn directly into silo 22 from the patient, thus eliminating exposure of tip 20 of needle 18 after the injection is completed. Of course, the biasing force provided by spring 40 is sufficient to overcome any forces tending to retain needle 18 within the patient.

Figure 5:
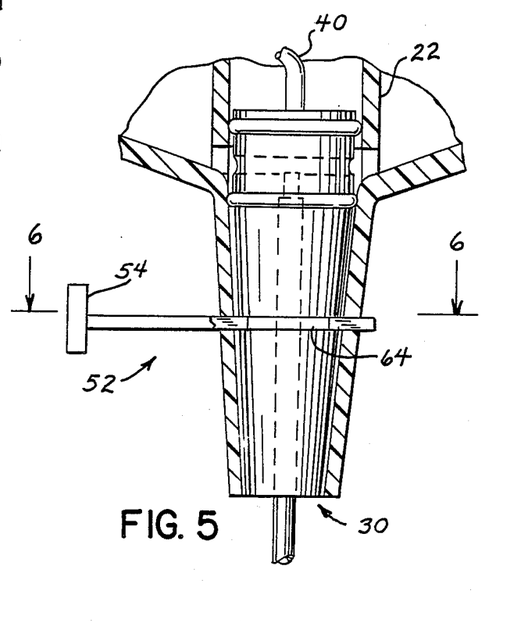
FIG. 5 is a detail view similar to FIG. 2, showing a slidable push button mechanism for retaining the needle in its extended position.
Figure 6:
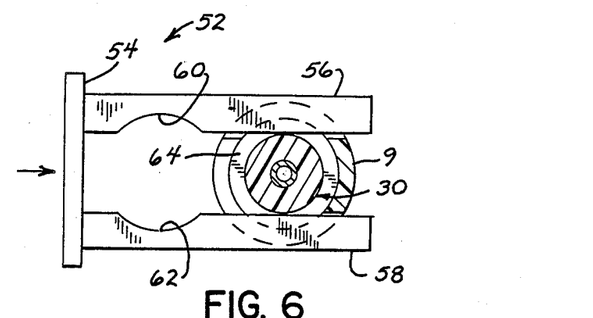
FIG. 6 is a sectional view taken generally along line 6—6 f FIG. 5 showing the push button mechanism of FIG. 5 retaining the needle in its extended position.
Figure 7:
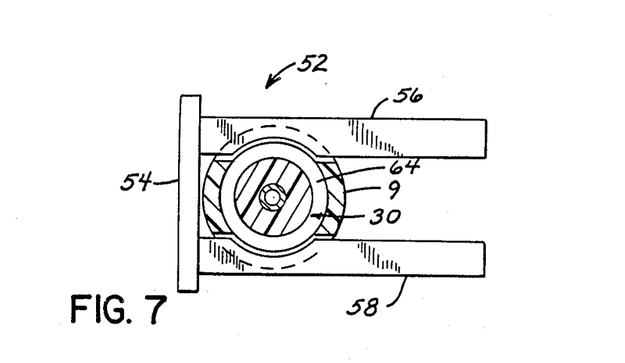
FIG. 7 is a view similar to FIG. 6, showing the push button mechanism of FIG. 5 moved to a release position for allowing the needle to retract.

Another embodiment of the invention is shown in FIGS. 5-7. In this embodiment, a push button mechanism is provided for retaining needle assembly 16 in its armed condition and for releasing needle assembly 16 for withdrawal into silo 22. A push button actuator 52 has a button end 54 with a pair of parallel legs 56, 58 extending therefrom. Legs 56, 58 have arcuate indentations 60, 62, respectively, formed therein. A slot 64 is provided about the periphery of head portion 30 of needle assembly 16. To retain needle assembly 16 in its extended position, the outer ends of legs 56, 58 engage slot 64 against the bias of spring 40. To release needle assembly 16, button 54 is pushed inwardly toward nipple 9 to position arcuate indentations 60, 62 adjacent slot 64, as shown in FIG. 7. In this manner, arcuate indentations 60, 62 create an opening of sufficient size to allow head portion 30 of needle assembly 16 to pass therebetween. The bias of spring 40 then draws needle assembly 16 into silo 22 to disarm syringe 2. As described above, this retraction of needle assembly 16 into silo 22 may be accomplished either before or after withdrawal of needle 18 from the patient.

Figures 8, 9:
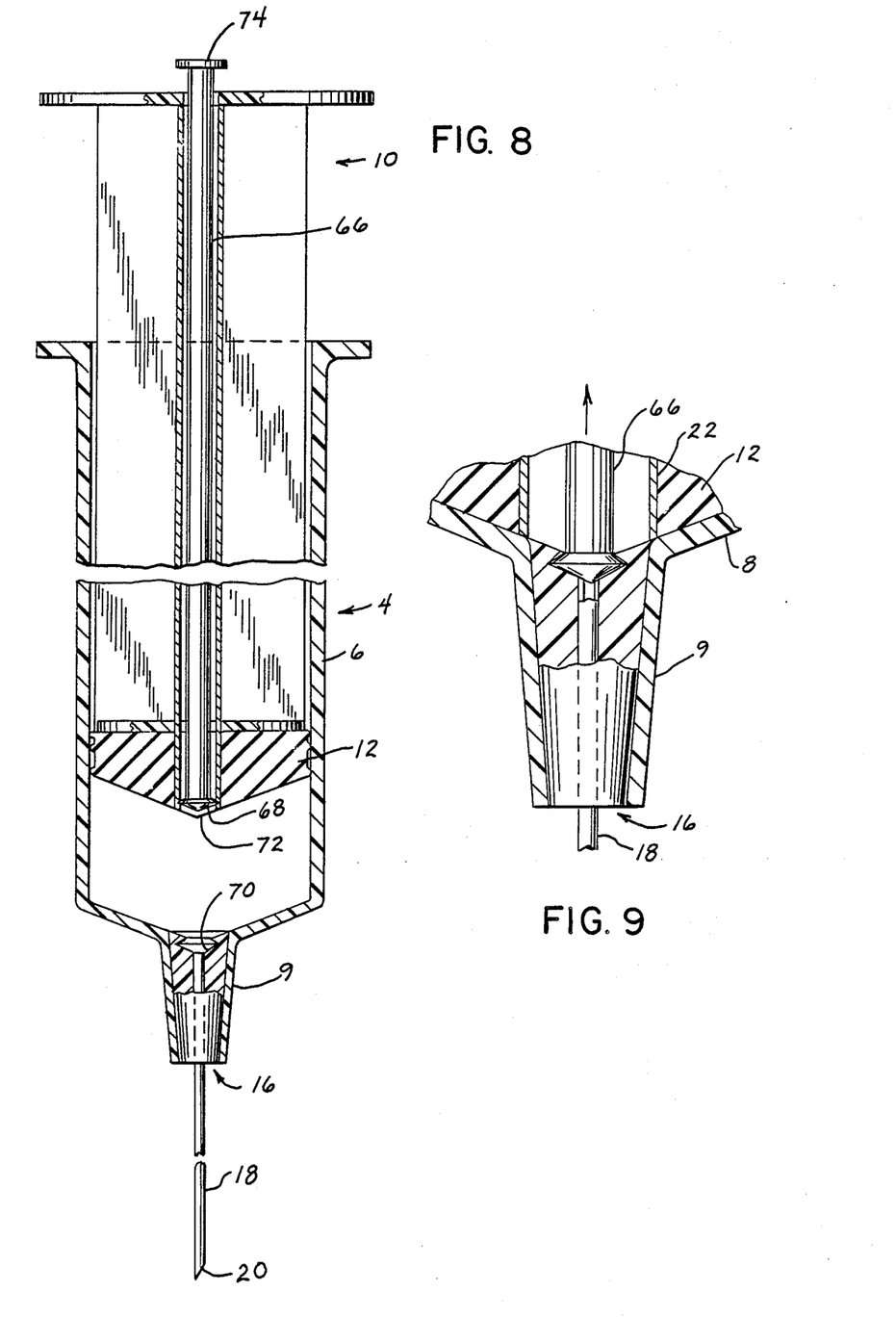
FIG. 8 is a view similar to FIG. 1, showing a manual retraction mechanism for withdrawing the needle into its retracted position.
FIG. 9 is a detail view of a portion of the syringe of FIG. 8, showing the manual retraction mechanism engaging the needle head prior to retraction of the needle.

Another embodiment of the invention is shown in FIGS. 8 and 9. In this embodiment, a retractable rod 66 extends longitudinally along the length of plunger assembly 10. Retractable rod 66 has an end portion 68, formed so as to mate with a receiving portion 70 formed in the upper end of needle head portion 30. A membrane 72 is provided over the end of head 12 of plunger assembly 10. In this embodiment, medication is administered by depressing plunger 10 to force medication through receiver 70 and into the longitudinal passage of needle 18. After medication has been so administered, head 12 of plunger assembly 10 is completely depressed so that membrane 72 is in contact with the inner surfaces of end wall 8 of body portion 4. A button 74 on the end of rod 66 is then depressed to move rod 66 downwardly so as to puncture membrane 72 and engage end portion 68 of rod 66 with receiving portion 70, as shown in FIG. 9. Thereafter, retractable rod 66 is manually drawn upwardly to withdraw needle assembly 16 into silo 22. Again, such retraction of needle assembly 16 may be accomplished either before or after withdrawal of needle 18 from the patient.

Figures 10, 11, 12:
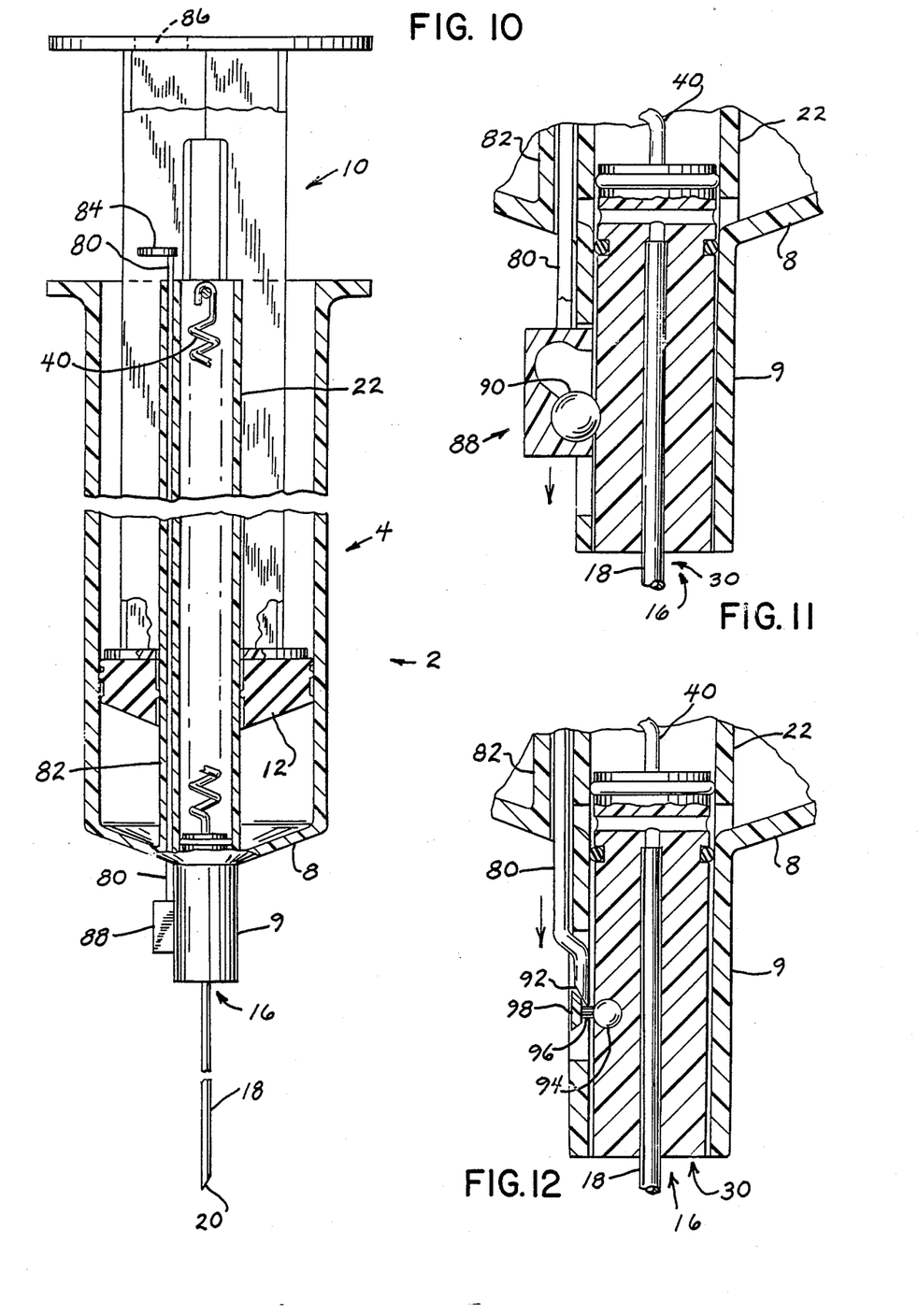
FIG. 10 is a view similar to FIG. 1, showing an auxiliary rod for effecting movement of a ball and socket type detent for allowing the needle to retract.
FIG. 11 is a detail view similar to FIG. 2, showing the interaction of the auxiliary rod with the ball and socket type detent.
FIG. 12 is a view similar to FIG. 2, showing a severable stem embodiment for the releasable retainer means of the invention.

In accordance with another embodiment of the invention, as shown in FIGS. 10 and 11, an actuator rod 80 extends along the length of body portion 4 of syringe 2 in a passage formed along silo 22 by means of a wall 82 connected to silo 22. The upper end of actuator rod 80 is provided with a button 84. An opening 86 is formed in the top of plunger assembly 10, of sufficient size to accommodate passage of button 84 provided on the upper end of actuator rod 80 therethrough. The lower end of actuator rod 80 is placed adjacent to and in contact with the upper edge of a movable ball-type detent 88. As shown in FIG. 11, the interior of movable ball-type detent 88 is provided with a pair of adjacent and adjoining internal sockets, both of which are adapted to receive a ball 90 therein The lowermost socket retains ball 90 in frictional engagement with the side portion of needle head portion 30, to frictionally engage needle head portion 30 and retain needle 18 in its extended position.

In this embodiment, plunger assembly 10 is depressed to eject fluid from the interior of body portion 4 of syringe 2, as is well known. When head portion 12 of plunger assembly 10 approaches end wall 8 of body portion 4, wherein substantially all of the medication contained within the interior of body portion 4 has been ejected therefrom, button 84 passes through opening 86 so that the upper surface of button 84 is substantially flush with the upper surface of plunger assembly 10. In this event, button 84 is engaged by the user during depression of plunger assembly 10 to eject the remainder of the medication from the interior of body portion 4. During the final ejection of medication, button 84 is depressed along with plunger assembly 10, thus moving actuator rod 80 downwardly. Such downward movement of actuator rod 80 also causes downward movement of movable ball-type detent 88. Upon downward movement of detent 88, ball 90 moves into the uppermost socket provided in detent 88, which is formed so as to release the frictional engagement of the side of needle head portion 30 to allow the needle assembly 16 to be withdrawn into silo 22 by the biasing force provided by spring 40. As with the previously described embodiments, the embodiment of FIGS. 10 and 11 includes passages in the lower end of silo 22 and in the upper end of needle head portion 30 to allow flow of medication from the interior of body portion 4 through needle 18. O-rings are provided in the upper portion of needle head portion 30 to prevent leakage of medication from the flow path.

A further embodiment, which is a variation on the embodiment of FIGS. 10 and 11, is shown in FIG. 12. In the embodiment of FIG. 12, the lower end of actuator rod 80 is provided with a sharpened tip 92. A ball 94 is disposed within a cavity provided in head portion 30 of needle assembly 16. A stem portion 96 extends between ball 94 and a cross-member 98, which spans across an opening formed in nipple 9. In this embodiment, upon depression of button 84 at the upper end of actuator rod 80, sharpened tip 92 at the lower end of actuator rod 80 moves downwardly so as to sever stem 96. Such severance of stem 96 takes place after medication has been completely ejected from the interior of body portion 4. Upon severance of stem portion 96, needle assembly 16 is allowed to retract into silo 22 by the force of spring 40 to disarm syringe 2. As with the previously described embodiments, passages are provided in the lower end of silo 22 and in the upper portion of needle head portion 30 to accommodate passage of medication from the interior of body portion 4 through needle 18. O-rings are provided to seal against leakage of medication.

Figures 13, 14:
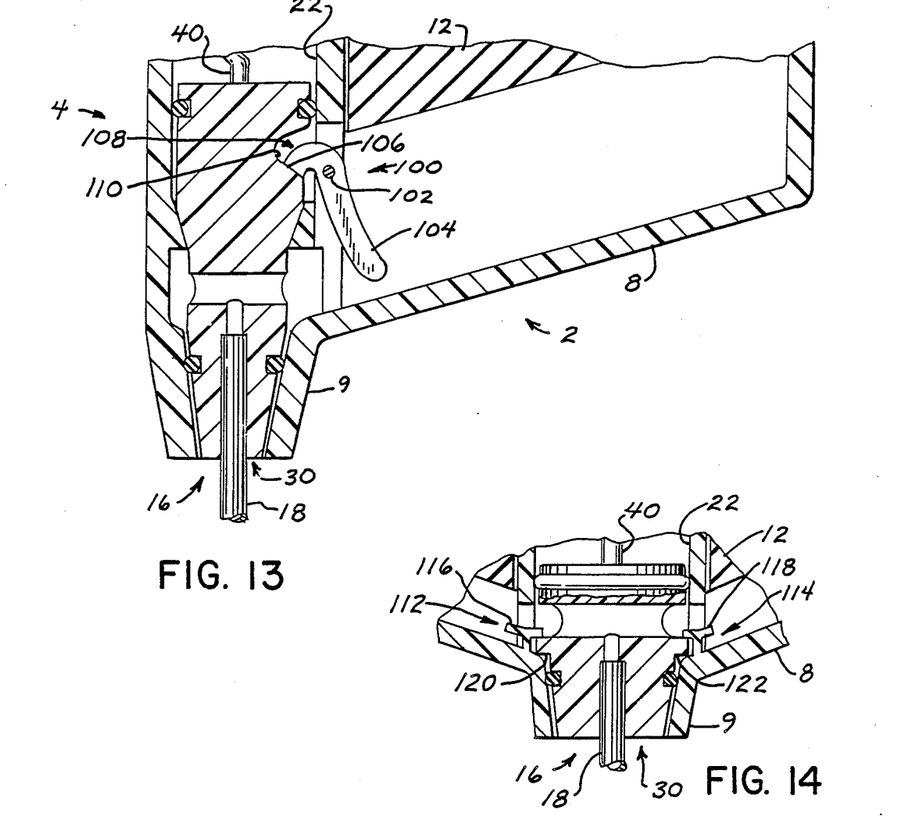
FIG. 13 is a view similar to FIG. 2, showing an automatic releasable retainer mechanism for releasing the needle upon depression of the plunger.
FIG. 14 is a detail view similar to FIG. 2, showing another automatic releasable retainer mechanism for releasing the needle upon depression of the plunger.
Figure 15:
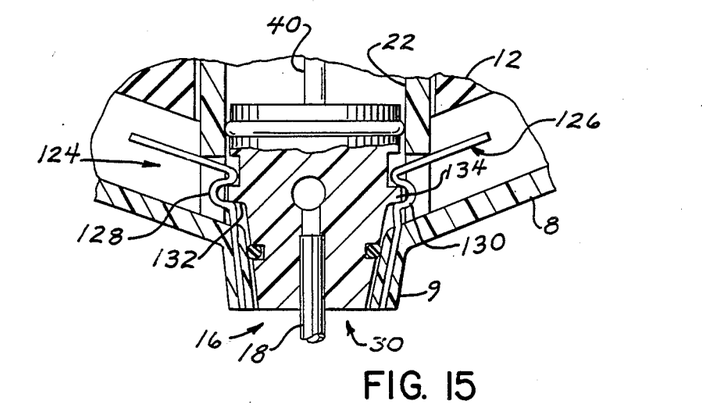
FIG. 15 is a detail view similar to FIG. 2, showing yet another automatic releasable retainer mechanism for releasing the needle upon depression of the plunger.

Further embodiments of the invention are shown in FIGS. 13-15. These embodiments provide automatic retraction of needle assembly 16 upon downward movement of plunger assembly 10 at a predetermined point in the interior of body portion 4 of syringe 2. With reference to FIG. 13, nipple 9 is disposed adjacent one side of body portion 4 of syringe 2 Silo 22 extends upwardly into the interior of body portion 4 from nipple 9 adjacent the same side of body portion 4 as nipple 9. A lever 100 is provided in an opening formed at the lower end of silo 22 adjacent end wall 8 of body portion 4. Lever 100 is pivotable about a pin 102 extending between the sides of the opening formed in the lower end of silo 22. Lever 100 has a trigger end 104 and a needle-engaging end 106. Head portion 30 of needle assembly 16 is provided with a detent depression 108 having an engagement surface 110, which is adapted to be engaged by needle-engaging end 106 of lever 100. A torsion spring or other similar mechanism (not shown) is provided at pin 102 to retain lever 100 in its needle engaging position shown in FIG. 13, wherein needle assembly 16 is retained in its extended position.

In operation, needle assembly 16 is released automatically upon depression of head portion 12 of plunger assembly 10 to a certain point. When head portion 12 is moved downwardly so as to move trigger end 104 of lever 100 leftwardly, lever 100 pivots clockwise about pin 102. Such pivoting of lever 100 moves needle-engaging end 106 rightwardly to release engagement surface 110 formed in head portion 30 of needle assembly 16. Such movement of ever 100, which takes place preferably after all medication within the interior of body portion 4 is ejected therefrom, allows needle assembly 16 to be retracted into silo 22 by the force of spring 40, to disarm syringe 2. As with the previously-described embodiments, passages are provided in needle head portion 30 and the lower end of silo 22 to allow medication to pass from the interior of body portion 4 through needle 18. O-rings are provided for sealing against leakage of medication.

Yet another automatic disarming system is shown in FIG. 14. In this system, a pair of upstanding flexible catch members 112, 114 are formed on the inner surface of end wall 8. Catch members 112, 114 have laterally extending upper portions 116, 118, respectively, the inner ends of which engage a pair of ears 120, 122 formed on head portion 30 of needle assembly 16 to retain needle assembly 16 in its extended position. Upon downward movement of plunger head 12, the lower surface of plunger head 12 contacts the outer ends of laterally extending upper portions 116, 118 of catch members 112, 114. Continued downward movement of plunger head 12 pivots catch members 112, 114 outwardly to release the engagement of ears 120, 122 by the inner ends of laterally extending upper portions 116, 118 of catch members 112, 114. Such outward flexing of catch members 112, 114 is accomplished after substantially all of the medication has been ejected from the interior of body portion 4 of syringe 2. As with the previously described embodiments, passages are provided in the lower end of silo 22 and in the upper portion of needle head portion 30 to allow medication to pass from the interior of body portion 4 through needle 18. O-rings are provided to seal such passage of medication against leakage.

Another embodiment of an automatic retraction system is shown in FIG. 15. In this embodiment, a pair of flexible wings 124, 126 are provided adjacent end wall 8 of body portion 4 and are anchored thereto, such as by embedment within the upper portion of nipple 9, as shown. Flexible wings 124, 126 have retaining portions 128, 130 formed therein which engage a pair of ears 132, 134 formed on head portion 30 of needle assembly 16. Retaining portions 128, 130 engage ears 132, 134 to retain needle assembly 16 in its extended position. Upon downward movement of plunger assembly 10 and head 12, the lower surface of plunger head 12 comes into contact with flexible wing members 124, 126. Upon continued downward movement of plunger head 12, flexible wings 124, 126 are depressed downwardly and outwardly so as to release retaining portions 128, 130 from engagement with ears 132, 134. Such release of ears 132, 134 allows needle assembly 16 to be retracted upwardly into silo 22 by the force of spring 40. The release of ears 132, 134 is accomplished after head portion 12 of plunger assembly 10 has moved downwardly toward end wall 8 a sufficient amount to eject substantially all of the medication from the interior of body portion 4. As with the previous embodiments, passages are provided in the lower end of silo 22 and the upper portion of needle head 30 to allow medication to flow from the interior of body portion 4 through needle 18. O-rings are provided in needle head portion 30 to seal against leakage of medication.

It is understood that a variety of mechanisms are contemplated for providing automatic retraction of the needle assembly after use of the needle. For example, and without limitation, withdrawal of the needle assembly in response to movement of the plunger may be caused by the presence or absence of a magnetic force, by attaining a certain predetermined hydrostatic pressure in the interior of the syringe, by the plunger releasing a thether retaining the needle in its extended condition, or by rotational movement of either the plunger or needle to effect release of the needle.

It is contemplated that the upper end of silo 22 can be sealed and a disinfectant provided in the interior of silo 22. This provides neutralization of any contamination present on needle 18 when needle assembly 16 is retracted.

Further, it is contemplated that needle assembly 16 can be in its retracted position during transportation, shipping and storage, and deployed into its extended position for arming syringe 2 for use. Thereafter, needle assembly 16 is retracted into silo 22 to disarm syringe 2.

FIGS. 16-22 disclose further embodiments of the invention, wherein a telescoping segmental sheath is adapted to extend over the needle after use to enclose its sharpened tip. The embodiments of FIGS. 16-22 will be described with reference to a myelographic needle, but it is understood that such embodiments are equally and effectively applicable to any needle adapted for use with a syringe.

Figures 16, 17, 18, 19:
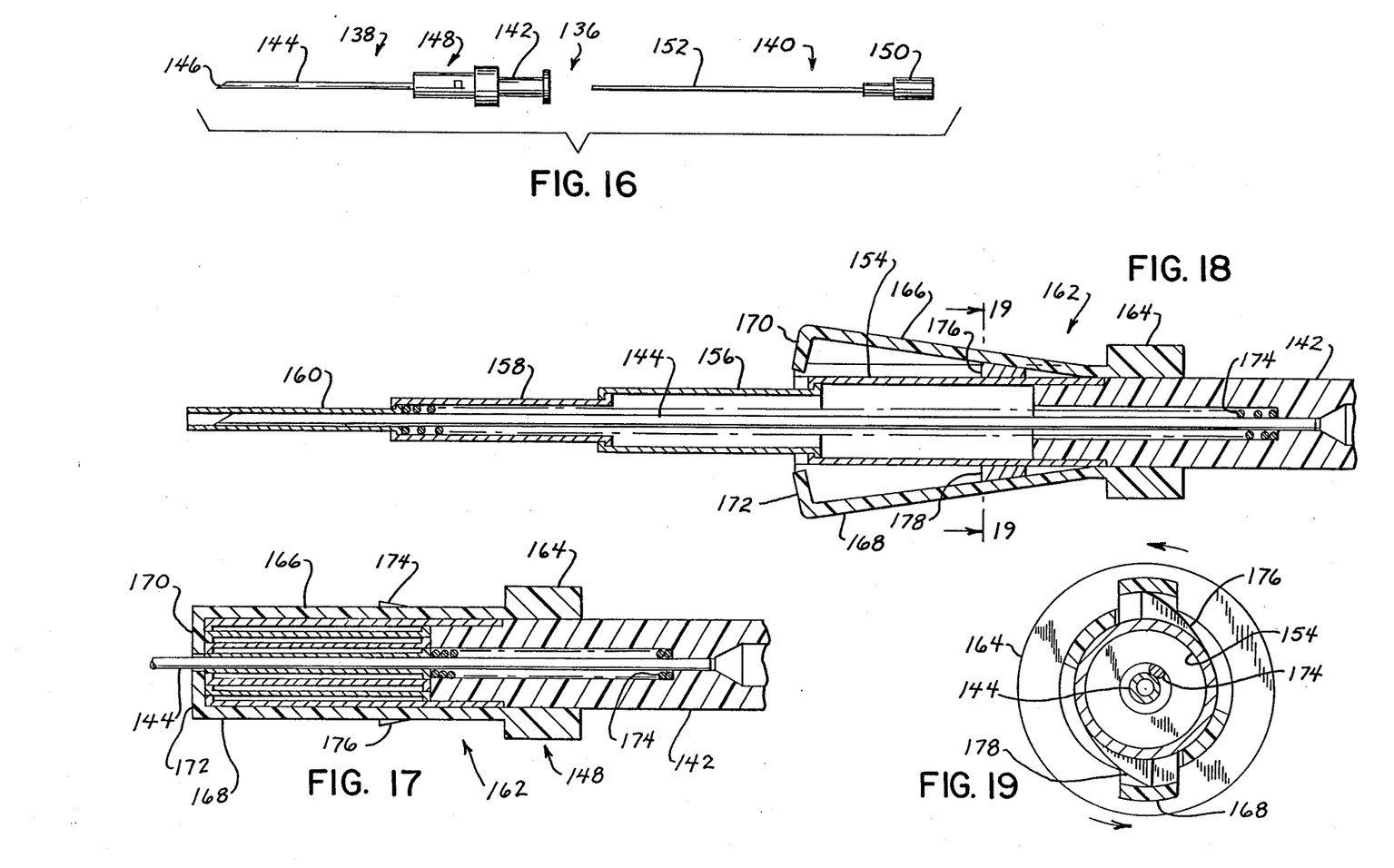
FIG. 16 is an exploded view of a myelographic needle fitted with a retracted telescoping sheath adapted to extend outwardly to cover the needle after use.
FIG. 17 is a detail view of the myelographic needle of FIG. 16, showing the telescoping sheath in its retracted position.
FIG. 18 is a detail view showing the telescoping sheath in its extended position.
FIG. 19 is a section view taken generally along line 19—19 of FIG. 18.

As shown in FIG. 16, a myelographic injection assembly 136 generally includes a needle portion 138 and an insert portion 140. Needle portion 138 has a hub 142 from which a needle 144 having a sharpened end 146 extends therefrom. An extendible segmental telescoping sheath, shown generally at 148, is connected to hub 142. Insert 140 has a head portion 150 and a plug portion 152. Head portion 150 is adapted to mate with an opening provided in the end of hub 142 of needle portion 138, with plug portion 152 extending throughout the length of needle portion 138 so as to plug the passage provided in needle 144 during insertion of the myelographic injection assembly 136 into the patient. Plug 152 prevents the passage of any tissue into the interior of the spinal cord during insertion of the myelographic injection assembly 136. After insertion of myelographic injection assembly 136 into the patient, insert portion 140 is withdrawn from needle portion 138 to allow a myelographic injection, as is well known.

FIG. 17 shows extendible segmental sheath 148 in its unextended or retracted condition, wherein needle 144 is exposed for use. Sheath 148 includes a plurality of telescoping segments 154, 156, 158 and 60, best shown in FIG. 18. Segments 154-160 are provided with cooperating inwardly and outwardly extending flanges which engage each other upon extension of sheath 148 to form the telescoping sheath assembly as shown in FIG. 18.

A retainer mechanism 162 retains telescoping sheath 148 in its retracted condition. Retainer mechanism 162 includes a ring 164 provided at hub 142 of needle portion 138. Ring 164 has a pair of arms 166, 168 extending therefrom. Arms 166, 168 are provided at their ends with inwardly extending fingers 170, 172, respectively. When myelographic injection assembly 136 is in its armed condition, wherein needle 144 is exposed for use, fingers 170, 172 engage the end portions of telescoping segments 154-160 to retain the segments in their retracted position. A biasing means, such as a compressed coil spring 174, is provided within a circumferential passage formed in hub 142 about needle 144. Coil spring 174 bears at one end against the end of the circumferential passage in hub 142, and at the other end against the inner end of telescoping segment 160. When telescoping sheath 148 is in its retracted position as shown in FIG. 17, telescoping segments 154, 160 are retained in position by retainer mechanism 162 against the force of coil spring 174.

To release telescoping sheath 148, ring 164 is turned counterclockwise, as shown in FIG. 19. Such clockwise turning of ring 164 causes arms 166, 168 to engage a pair of ramps 176, 178 formed on sheath segment 154. Such engagement of arms 166, 168 with ramps 176, 178 causes arms 166, 168 to move outwardly, as shown in FIGS. 18 and 19. Such outward movement of arms 166, 168 causes fingers 170, 172 to likewise move outwardly to release the ends of telescoping segments 154-160 and to cause telescoping sheath 148 to move to its extended position, shown in FIG. 18, by means of the biasing force provided by spring 174. As with the previously described embodiments of the invention, the counterclockwise rotation of ring 164 may be performed by the person administering the injection either while needle 144 is still in place in the patient or after needle 144 has been withdrawn.

Figure 20:
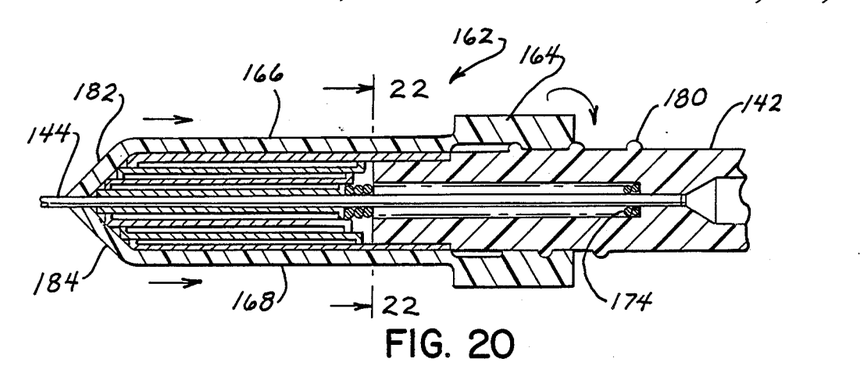
FIG. 20 is a detail view similar to FIG. 18, showing another embodiment of the releasable retainer means for retaining the telescoping sheath on a myelographic needle.
Figure 21:
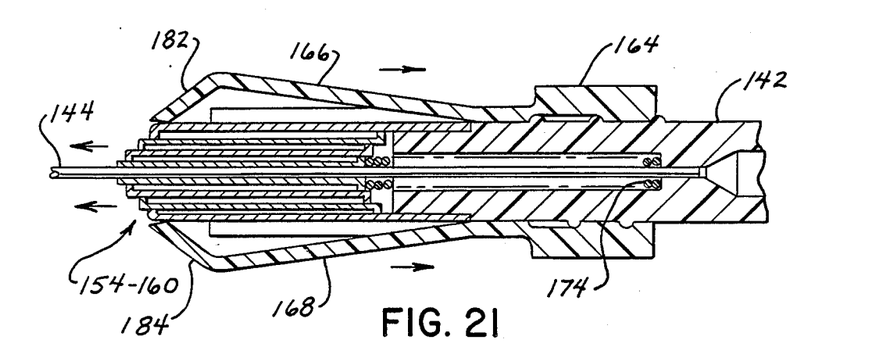
FIG. 21 is a view similar to FIG. 20, showing the releasable retainer mechanism of FIG. 20 in a release position for allowing the telescoping sheath to extend outwardly so as to cover the needle.
Figure 22:
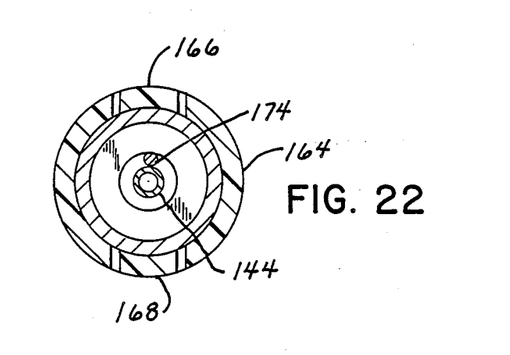
FIG. 22 is a section view taken generally along line 22—22 of FIG. 20.

FIGS. 20-22 show another embodiment for the telescoping sheath disabling mechanism of the present invention. In this embodiment, ring 164 of retainer mechanism 162 again has arms 166, 168 extending therefrom. Hub 142 of needle portion 138 is provided with a series of external threads 180, and ring 164 is provided with a series of internal threads adapted to mate with external threads 180. In this embodiment, arms 166, 168 have inwardly extending angled fingers 182, 184 which retain telescoping segments 154-160 in their retracted position against the force of spring 174. Angled fingers 182, 184 extend from the ends of arms 166, 168 at an obtuse angle thereto. After the injection has been completed, ring 164 is turned on threads 180 of hub 142 so as to move rightwardly. Such movement of ring 164 causes angled fingers 182, 184 to ride up on the leftward ends of telescoping segments 154-160 so as to release telescoping segments 154-160, as shown in FIG. 21. This release of engagement of fingers 182, 184 with the end portions of segments 154-160 allows the biasing force provided by spring 174 to project telescoping segments 154-160 outwardly to cover needle 144. Again, this can occur either while needle 144 is still in the patient or after needle 144 has been withdrawn from the patient.

It is understood that the telescoping sheath arrangement for enclosing the needle after use may be utilized in connection with an automatic or semi-automatic triggering mechanism provided on the syringe, as opposed to on the needle assembly itself.

The present invention provides a medical syringe which, after actuation of the disarming mechanism, is practically not reusable without destruction of the syringe. This feature of the invention is advantageous in that it prevents contact with the needle after use, whether intentional or inadvertent, thus preventing the spread of any infection present on the needle from the patient.

Various alternatives and modifications are contemplated as being with the scope of the following claims particularly pointing out and distinctly claiming the invention.

We claim:

1. A syringe, comprising:

a body portion for holding fluid;

a hollow needle interconnected with said body portion for transferring fluid between said body portion and a patient, said needle having a head portion and a sharpened tip, said needle being movable between an extended position in which said sharpened tip projects outwardly from said body portion and said head portion is positioned such that the interior of said hollow needle is in communication with the interior of said body portion, and a retracted position in which the sharpened tip of said needle is enclosed;

a plunger associated with said body portion for ejecting fluid through said needle from the interior of said body portion of drawing fluid through said needle into the interior of said body portion;

a protective sheath associated with said syringe into which needle is withdrawn into its retracted position after use for enclosing the tip of said needle to prevent accidental contact therewith;

disarming means associated with said syringe for disarming said needle after use by moving said needle from its extended position to its retracted position, said disarming means including biasing means for biasing said needle toward its retracted position; and actuator means associated with said syringe and actuable by the user of said syringe for actuating said disarming means, said actuator means comprising releasable retainer means for retaining said syringe in an armed condition wherein said needle is in its extended position during use against the force of said biasing means, and wherein said releasable retainer means releases said needle upon actuation to withdraw said needle into said sheath by the force of said biasing means to convert said syringe to its disarmed condition to prevent accidental contact therewith, said releasable retainer means comprising a movable rod associated with said body portion of said syringe and movable ball-type detent means associated with said syringe for retaining said needle in its extended position against the biasing force of said biasing means during use, and wherein said rod is movable so as to effect movement of said ball-type detent mechanism, said movement of said ball-type detent mechanism effecting a release of said needle for allowing said needle to be withdrawn into said protective sheath by said biasing means after use to achieve said disarmed condition.

2. In a medical device for administering or receiving a fluid to or from a patient, said medical device including conduit means extending therefrom having a sharpened end adapted for insertion into said patient for allowing said fluid to flow between said medical device and said patient, and further including a fluid-containing cavity, the improvement comprising:

disarming means comprising a protective sheath disposed within said fluid-containing cavity for converting said medical device from an armed condition wherein said sharpened end of said conduit means is exposed, to a disarmed condition wherein said sharpened end of said conduit means is covered so as to prevent accidental contact therewith by enclosing the length of said conduit means within said protective sheath, said disarming means including means urging said medical device toward said disarmed condition; and releasable retainer means associated with said medical device for retaining said medical device in said armed condition prior to and during use, said releasable retainer means including a one-way lock for maintaining said medical device in said armed condition against the force of said means urging said medical device toward said disarmed condition, said one-way lock being actuable after use of said medical device for releasing said means urging said medical device toward said disarmed condition so as to cause said conduit means to be withdrawn into said sheath and to retain said conduit means therein to prevent reuse of said medical device.

3. The invention according to claim 2, wherein said means urging said medical device toward said disarmed condition comprises biasing means connected to said conduit means, said biasing means tending to draw said conduit means into said protective sheath.

4. The invention according to claim 2, wherein said releasable retainer means releases said conduit means upon actuation by the user, and comprises a pivotable catch associated with said medical device for engaging a detent formed on said conduit means, said pivotable catch retaining said medical device in its armed condition against said means urging said medical device toward said disarmed condition, said pivotable catch being actuatable by the user of said medical device to release said detent means formed on said conduit means to cause said means urging said medical device toward said disarmed condition to convert said medical device to said disarmed condition upon actuation thereof.

5. The invention according to claim 2, wherein said releasable retainer means releases said conduit means upon actuation by the user, and comprises a slidable mechanism associated with said medical device, said slidable mechanism engaging a detent means associated with said conduit means for retaining said medical device in its armed condition against said means urging said medical device toward said disarmed condition during use, and wherein said slidable mechanism is actuatable by the user by moving said slidable mechanism in a direction transverse to said medical device, said slidable mechanism including release means for disengaging said detent means when said slidable mechanism is moved in a direction transverse to said medical device to release said conduit means and to cause said conduit means to be withdrawn into said protective sheath after use by said means urging said medical device toward said disarmed condition.

6. In a medical device for administering or receiving a fluid to or from a patient, said medical device including conduit means extending therefrom having a sharpened end adapted for insertion into said patient for allowing said fluid to flow between said medical device and said patient, the improvement comprising:

disarming means comprising a protective sheath disposed within the interior of said medical device for converting said medical device from an armed condition wherein said sharpened end of said conduit means is exposed, to a disarmed condition wherein said sharpened end of said conduit means is covered so as to prevent accidental contact therewith by enclosing the length of said conduit means within said protective sheath, said disarming means including means urging said medical device toward said disarmed condition; and releasable retainer means associated with said medical device for retaining said medical device in said armed condition during use and for releasing said means urging said medical device toward said disarmed condition after use so as to cause said medical device to be converted to said disarmed condition, said releasable retainer means comprising a movable rod associated with said medical device and movable ball-type detent means associated with said medical device for retaining said medical device in its armed condition against said means urging said medical device toward said disarmed condition during use, and wherein said rod is movable so as to effect movement of said ball-type detent mechanism, said movement of said ball-type detent mechanism effecting a release of said conduit means for allowing said conduit means to be withdrawn into said protective sheath after use by said means urging said medical device toward said disarmed condition.

7. The invention according to claim 2, wherein said releasable retainer means releases said conduit means upon actuation by the user, and comprises a movable rod associated with said medical device and having a sharpened tip, said releasable retainer means further comprising a stem extending between said medical device and said conduit means for retaining said medical device in its armed condition against said means urging said medical device toward said disarmed condition during use, said stem being severable by said sharpened tip of said rod upon movement thereof to release said conduit means for allowing said conduit means to be withdrawn into said protective sheath after use by said means urging said medical device toward said disarmed condition.

8. The invention according to claim 2, wherein said releasable retainer means releases said conduit means upon actuation by a plunger associated with said medical device during downward movement of said plunger, and comprises a pivotable lever disposed adjacent the lower end of said protective sheath and being pivotably connected thereto, said pivotable lever including a conduit-engaging end and a trigger end, said conduit-engaging end engaging said conduit means for retaining said medical device in its armed condition against said means urging said medical device toward its disarmed condition during use, and wherein said trigger end of said lever is pivotable in response to downward movement of said plunger for releasing engagement of said conduit means by said conduit-engaging end to allow said conduit means to be withdrawn into said protective sheath after use by said means urging said medical device toward said disarmed condition.

9. The invention according to claim 2, wherein said releasable retainer means releases said conduit means upon actuation by a plunger associated with said medical device during downward movement of said plunger, and comprises one or more flexible catch members associated with said medical device for engaging said conduit means to retain said medical device in its armed condition against said means urging said medical device toward its disarmed condition during use, and wherein said catch members are adapted to flex upon engagement by said plunger and downward movement thereof to release said engagement with said conduit means for allowing said conduit means to be withdrawn into said protective sheath after use by said means urging said medical device toward said disarmed condition.

10. The invention according to claim 2, wherein said releasable retainer means releases said needle upon actuation by a plunger associated with said medical device during downward movement of said plunger, and comprises one or more flexible wings associated with said medical device for engaging said conduit means to retain said medical device in its armed condition against said means urging said medical device toward said disarmed condition during use, and wherein said flexible wings flex outwardly upon engagement by said plunger and downward movement thereof to release said engagement with said conduit means for allowing said conduit means to be withdrawn into said protective sheath after use by said means urging said medical device toward said disarmed condition.

11. A syringe, comprising:
a tubular body portion providing an internal fluid-containing cavity;
an axially extending sheath associated with said body portion;
a hollow needle interconnected with said syringe and having a head portion and a sharpened tip, said needle being movable between an extended position in which said sharpened tip projects outwardly from an end of said tubular body portion and the interior of said hollow needle is in communication with said body portion cavity, and a retracted position in which said needle is withdrawn into said sheath so as to enclose said sharpened tip for preventing accidental contact therewith;
a plunger interconnected with said syringe and having a head portion disposed within said body portion cavity, said head portion being movable within said body portion cavity for ejecting fluid therefrom or drawing fluid thereinto;
biasing means for urging said needle toward its retracted position;
one-way lock means movable between an engaging position and a release position, said one-way lock means retaining said needle in its extended position when in its engaging position against the force of said biasing means, and allowing said biasing means to move said needle to its retracted position when in its release position; and
actuator means actuable by a user after use of said syringe for moving said one-way lock means from its engaging position to its release position, for allowing said biasing means to move said needle to its retracted position after use, said needle thereafter being maintained within said sheath for preventing reuse of said syringe.

12. The syringe according to claim 11, wherein said biasing means comprises a stretched coil spring connected at one end to said needle head portion and connected at its other end to said syringe so as to be in a stretched condition when said needle is in its extended position, to create a biasing force tending to withdraw said needle into said sheath.

13. The syringe according to claim 11, wherein movement of said plunger triggers said actuator means so as to move said one-way lock means to its release position, thereby causing said needle to be moved to its retracted position.

14. The syringe according to claim 13, wherein downward movement of said plunger by a user causes downward movement of an actuator rod which acts to move said one-way lock means from its engaging position to its release position.

15. The syringe according to claim 14, wherein said one-way lock means comprises movable ball-type detent means associated with said syringe for retaining said needle in its extended position against the biasing force of said biasing means during use, and wherein downward movement of said actuator rod caused by downward movement of said plunger moves said ball-type detent means to said release position for releasing engagement of said ball-type detent means with said needle and allowing said needle to move to its retracted position.

16. In a syringe comprising a tubular body portion providing an internal fluid-receiving cavity and a plunger having a movable plunger head disposed within said body portion cavity, the improvement comprising:
an axially extending sheath disposed within said fluid-receiving cavity;
a hollow needle having a head portion and a sharpened tip, said needle being movable between an extended position in which said sharpened tip extends outwardly from an end of said tubular body portion and the interior of said hollow needle is in communication with said body portion cavity, and a retracted position in which said needle is withdrawn into said sheath for enclosing said sharpened tip for preventing accidental contact therewith;
biasing means for urging said needle toward its retracted position;
one-way lock means movable between an engaging position and a release position, said one-way lock means retaining said needle in its extended position when in its engaging position against the force of said biasing means, said one-way lock means allowing said biasing means to move said needle to its retracted position when in its release position; and
actuator means actuable by a user after use of said syringe for moving said one-way lock means from its engaging position to its release position for allowing said biasing means to move said needle to its retracted position after use, said needle thereafter being maintained within said sheath for preventing reuse of said syringe.

17. The improvement of claim 16, wherein movement of said plunger triggers said actuator means so as to move said one-way lock means to its release position, thereby causing said needle to be moved to its retracted position.

18. The improvement of claim 17, wherein downward movement of said plunger by a user causes downward movement of an actuator rod which acts to move said one-way lock means from its engaging position to its release position.

19. The improvement of claim 18, wherein said one-way lock means comprises movable ball-type detent means associated with said syringe for retaining said needle in its extended position against the biasing force of said biasing means during use, and wherein downward movement of said actuator rod caused by downward movement of said plunger moves said ball-type detent means to said release position for releasing engagement of said ball-type detent means with said needle and allowing said needle to move to its retracted position.

* * * * *

UNITED STATES PATENT AND TRADEMARK OFFICE
CERTIFICATE OF CORRECTION

PATENT NO. : 4,874,382

DATED : October 17, 1989

INVENTOR(S) : LINDEMANN ET AL

It is certified that error appears in the above-identified patent and that said Letters Patent is hereby corrected as shown below:

Claim 1, Col. 11, Line 25, After "portion" delete "of" and substitute therefor --- for ---;

Claim 1, Col. 11, Line 28, After "which" insert --- said ---

Signed and Sealed this

Twenty-first Day of May, 1991

Attest:

HARRY F. MANBECK, JR.

Attesting Officer

Commissioner of Patents and Trademarks